United States Patent [19]

Fourcadier et al.

[11] 4,314,810
[45] Feb. 9, 1982

[54] COMPOSITIONS SUITABLE FOR USE IN DYEING HAIR OBTAINED FROM THE REACTION OF A POLYHYDROXYBENZENE AND AN OXIDATIVE DYESTUFF PRECURSOR OF THE PARA TYPE

[75] Inventors: Chantal Fourcadier; Jean F. Grollier, both of Paris, France

[73] Assignee: L'Oreal, Paris, France

[21] Appl. No.: 61,035

[22] Filed: Jul. 26, 1979

[30] Foreign Application Priority Data

Jul. 27, 1978 [FR] France .............................. 78 22296

[51] Int. Cl.$^3$ .............................................. A61K 7/13
[52] U.S. Cl. ......................................... 8/410; 8/405; 8/429; 8/524
[58] Field of Search ...................... 8/10.2, 11, 32, 429, 8/405, 524, 410

[56] References Cited

U.S. PATENT DOCUMENTS

| | | | |
|---|---|---|---|
| 3,236,734 | 2/1966 | Charle et al. | 8/11 |
| 3,981,678 | 9/1976 | Ghilardi et al. | 8/524 |
| 4,054,413 | 10/1977 | Feinland et al. | 8/10.2 |

FOREIGN PATENT DOCUMENTS

| | | |
|---|---|---|
| 1310864 | 3/1973 | United Kingdom . |
| 1388240 | 3/1973 | United Kingdom . |
| 1489344 | 10/1977 | United Kingdom . |

*Primary Examiner*—Joseph L. Schofer
*Attorney, Agent, or Firm*—Fleit & Jacobson

[57] ABSTRACT

Process for the preparation of a composition suitable for use in dyeing human hair, which composition contains a mixture of dyestuff precursors obtained by reacting at least one polyhydroxybenzene of the formula:

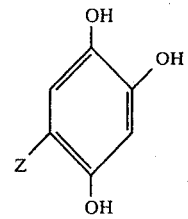

and one precursor of the formula:

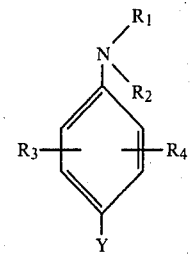

which process comprises the following stages:
(1) the abovementioned reaction is carried out in an anaerobic medium in a first solvent which is chosen with regard to the course of the reaction and the subsequent lyophilization;
(2) the reversible reaction is stopped at the desired stage by freezing; and
(3) the final reaction mixture is lyophilized with the removal of the first solvent. At the time of use
(4) the lyophilizate obtained in (3) is dissolved in a second solvent which is a cosmetic solvent suitable for hair dyeing and which can be different from the first solvent.

27 Claims, No Drawings

COMPOSITIONS SUITABLE FOR USE IN DYEING HAIR OBTAINED FROM THE REACTION OF A POLYHYDROXYBENZENE AND AN OXIDATIVE DYESTUFF PRECURSOR OF THE PARA TYPE

DESCRIPTION

The present invention relates to lyophilisates of mixtures of dyestuff precursors resulting from the reaction, in an anaerobic medium, of at least one polyhydroxybenzene and at least one "oxidative dyestuff precursor of the para type" or a derivative thereof, and also to the use of these lyophilisates in compositions for dyeing human hair; the term "oxidative dyestuff precursor" of the para type is understood as meaning compounds of the diamine or aminophenol type in which the functional groups are located in the para-position relative to one another.

French Pat. No. 1,222,700 discloses the preparation of leuco derivatives obtained by the reversible reaction, in solution in an anaerobic medium, of 1,2,4-trihydroxybenzene and a primary amine, the resulting leuco derivative subsequently being isolated and then used in a dyeing composition. The leuco derivative is oxidised on contact with the air during application to the hair, and this oxidation can be accelerated by the presence of an oxidising agent in the dyeing composition. This process produces shades and sheens which are of value for hair dyeing. However, in order to avoid a rather poor colour, it is frequently necessary to use several of the above-mentioned leuco derivatives, to add other dyestuffs thereto and/or to carry out several successive applications.

The use of a mixture resulting from the reaction of polyhydroxybenzenes and primary, or even secondary, amines, rather than the use of the leuco derivative isolated beforehand, has also been proposed. However, in this case, it is never certain whether the final stage of the equilibrium of the reversible reaction, or a well-defined intermediate stage, will be reached; also the final reaction mixture only contains two air-oxidisable dyestuff precursors of value, namely, on the one hand, the polyhydroxybenzene, and, on the other hand, the leuco derivative which imparts, in particular on oxidation, the sheen of the coloration. The uncertainty is further increased when the packaged reaction solution is stored, possibly for several months, with the result that, on application to human hair, the results obtained can show substantial variations in the shade.

In such known systems, the solvents used as a carrier for the reaction medium also constitute the carrier for the dyeing composition, and it is difficult to find a single solvent which is compatible both with the desired course of the reversible reaction and with a satisfactory absorption of the dyestuffs on the keratin fibres at the time of application.

In fact, dyestuff precursors such as polyhydroxybenzenes and oxidative dyestuff precursors of the para type generally have good solubility, in particular, in water, whilst their reaction products, that is to say leuco derivatives and oxidation products of leuco derivatives, are more soluble in organic solvents. As a result, it is necessary to find a compromise and to choose a solvent or a mixture of solvents, and also concentration levels of these solvents, which satisfy the requirements of, on the one hand, the desired displacement of the equilibrium of the reversible reaction, and, on the other hand, the production of a satisfactory dye under the conditions of application to the hair. The low concentrations of reactants and leuco derivatives which are necessary if any undesirable precipitation of the dyestuff principles is to be avoided, explain why such dyeing compositions frequently have a low dyeing strength; this is the case, in particular, with the compositions described in DOS (German Published Specification) No. 2,532,036.

The poor colours obtained using such reaction mixtures occur when these mixtures reach a stage approaching the final equilibrium stage of the reversible reaction, this being most frequently the case because of the fact that the packaged dyeing compositions are stored for a period of time which can extend to several months.

We have now discovered, according to the present invention, that the disadvantages inherent in the preparation of mixtures of dyestuff precursors resulting from the reaction, in an anaerobic medium, of at least one polyhydroxybenzene and at least one oxidative dyestuff precursor of the para type can be reduced or overcome by stopping the reaction at a desired and well-controlled stage of the reversible reaction, using a lyophilisation technique. Lyophilisation involves a freezing treatment which makes it possible to stop the reversible reaction at any desired stage, and this eliminates any uncertainty as regards the proportions of the reactants present and of the reaction product.

Moreover, this process, which involves the removal of the solvent, makes it possible to use, in the reaction, a solvent which assists the displacement of the equilibrium in a desired manner, without this solvent necessarily being compatible with the requirements of dyeing live human hair, and, in particular, the requirements of absorbing the dyestuff on the keratin fibres. It is therefore possible to choose, for the reaction mixture, a solvent which need only satisfy the best conditions required for the course of the reversible reaction and the subsequent lyophilisation treatment. Thus, the solvent can, for example, be chosen so that the reaction takes place in a homogeneous liquid phase, that is to say in the absence of any precipitate, and even so that it takes place at an elevated temperature and for a prolonged period of time, without taking account of any consideration of a cosmetic nature, both as regards the solvent itself and the conditions for its use.

The lyophilisate can then be dissolved in another solvent which, in this case, is a "cosmetic" solvent which can be chosen solely for its properties in relation to dyeing hair.

Finally, the blocking of the reaction at an intermediate stage makes it possible to increase the range of shades of the mixture of dyestuff precursors, which mixture, in this lyophilised form, can contain, on the one hand, the initial reactants, and, on the other hand, the leuco derivatives formed, in particularly valuable proportions.

The present invention provides a process for the preparation of a dyeing composition which composition contains a mixture of dyestuff precursors, obtained by reacting at least (a) one polyhydroxybenzene and at least (b) one oxidative dyestuff precursor of the para type, which process comprises the following stages:
 (1) the abovementioned reaction is carried out in an anaerobic medium in a first solvent which is chosen with regard to the course of the reaction and the subsequent lyophilisation;

(2) the reversible reaction is stopped at the desired stage by freezing;

(3) the lyophilisation and the desorption of the final reaction mixture are carried out with the removal of the first solvent; and (4) the lyophilisate obtained in (3) is dissolved, at the time of use, in a second solvent which is a solvent suitable for use in hair dyeing and which can, in particular, be different from the first solvent.

The invention also provides the lyophilised powders prepared in stage (3) and composite powders resulting from the association of a lyophilised powder or several lyophilised powders, according to the invention, with other lyophilisates and also with direct dyestuffs or other cosmetic ingredients in the pulverulent form.

According to a preferred embodiment of the invention, (a) at least one polyhydroxybenzene having the formula

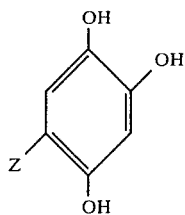

(I)

in which Z denotes an alkoxy or alkyl radical or a hydrogen atom, is reacted, at a pH of 3 to 11, preferably 5 to 9, optionally in the presence of compatible cosmetic ingredients, in an anaerobic medium, with (b) at least one oxidative dyestuff precursor of the para type, having, in particular, the formula:

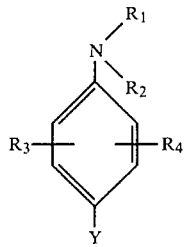

(II)

in which:

Y denotes: either a group OH, if $R_1$, $R_2$ and $R_3$ simultaneously denote a hydrogen atom, it being possible for $R_4$ to denote a hydrogen atom or an alkyl radical, or Y denotes an $NH_2$ group, if:

$R_1$ and $R_2$, which are identical or different, denote a hydrogen atom or an alkyl, hydroxyalkyl or alkoxyalkyl radical, or $R_1$ denotes a hydrogen atom or an alkyl radical and $R_2$ denotes an alkoxy, carbamylalkyl or mesylaminoalkyl radical, an aminosulphonylalkyl radical in which the nitrogen atom is optionally substituted, a piperidinoalkyl or morpholinoalkyl radical or a phenyl nucleus, or $R_1$ and $R_2$ form, together with the nitrogen atom to which they are attached, a heterocyclic ring such as piperidino or morpholino;

$R_3$ denotes a hydrogen atom, an alkyl radical or the radical —$OR_5$, in which $R_5$ represents a hydroxyalkyl or alkoxyalkyl group; and $R_4$ denotes a hydrogen atom or an alkyl radical.

It is also possible to use a salt of these oxidative dyestuff precursors, such as a hydrochloride, sulphate, acetate, citrate or tartrate; the alkyl radicals or the alkyl part of the radicals in the above-mentioned definitions of formulae I and II preferably contain 1 to 4 carbon atoms.

A variety of different solvents can be used as the carrier for the reaction medium, depending on the stage of equilibrium of the reversible reaction which it is desired to achieve, and depending on the solubility of the initial reactants and also of the reaction products. In particular, the reaction can be carried out in a homogeneous liquid phase or also in a heterogeneous phase, in the presence of a solvent only for the initial reactants, which displaces the equilibrium in the direction for the production of the leuco derivative which is insoluble in this solvent. The following solvents may be mentioned as solvents used in stage (1): dioxane, an alknol such as tert.-butyl alcohol, benzyl alcohol, cyclohexanol, or mixtures thereof, and solvents which do not give eutectics with water.

A reaction mixture is thus obtained which contains at least one polyhydroxybenzene, one oxidative dyestuff precursor of the para type and one leuco derivative, in proportions depending on the reaction time, which varies from a few hours e.g. 3 hours to several weeks, e.g. 5 weeks, and on the reaction temperature, which varies from, for example, 10° C. to the reflux temperature of the solvent; however, a temperature of 20° to 50° C. is peferably used.

1,2,4-Trihydroxybenzene, 2,4,5-trihydroxytoluene and 5-methoxy-1,2,4-trihydroxybenzene may be mentioned as examples of compounds of formula I.

Examples which may be mentioned of oxidative dyestuff precursors of the para type of formula II, which can be used are: N,N-bis-(β-hydroxyethyl)-para-phenylenediamine, para-aminophenol, para-phenylenediamine, para-toluylenediamine, 2,6-dimethyl-para-phenylenediamine, 2,5-diaminophenoxyethanol, 2,5-diaminophenyl β-methoxyethyl ether, para-aminodiphenylamine, N-(β-methoxyethyl)-para-phenylenediamine, N-(β-hydroxyethyl)-para-phenylenediamine, N-(β-diethylaminosulphonylethyl)-para-phenylenediamine, N,N-dimethyl-para-phenylenediamine, N-ethyl-N-carbamylmethyl-para-phenylenediamine, N-ethyl-N-mesylaminoethyl-para-phenylenediamine, N-ethyl-N-(β-piperidinoethyl)-para-phenylenediamine, 3-methyl-N-ethyl-N-carbamylmethyl-para-phenylenediamine, 3-methyl-N-ethyl-N-(β-mesylaminoethyl)-para-phenylenediamine, N-(para-aminophenyl)-morpholine, N-(para-aminophenyl)-piperidine and N-methyl-paraphenylenediamine and their corresponding salts.

In order to protect the reactants and the products during lyophilisation and improve the storage of the final lyophilisate, reducing agents can be incorporated in the reaction mixture, and, optionally, in the final lyophilisate, at concentrations of, say, 0.01 to 5% by weight, at the start or at the end of the condensation reaction.

Amongst these reducing agents, there may be mentioned, in particular: dithionite and also the bisulphite or sulphite of sodium, potassium or ammonium, ascorbic acid, its esters and its salts, formamidine-sulphinic acid, thiomalic acid and cysteine and its salts.

At the end of the reaction and before lyophilisation, it is also possible to lower the pH of the reaction mixture to a pH of, say, 2 to 3 using a solid acid such as citric, maleic or tartaric acid.

According to an advantageous variant, in order to obtain a lyophilisate which has improved texture and an increased solubility at the time of use in the dyeing carrier, an inorganic or organic filler, which is chemically inactive with respect to the constituents of the mixture, can be added to the reaction mixture, in an amount of up to, say 20% by weight, at the start or at the end of the reaction.

A filler which is soluble in the reaction medium and of low hygroscopicity is preferably used, such as cosmetic ingredients including aminoacids or polypeptides; casein hydrolysates; carbohydrates, such as glucose, lactose, sorbitol and maltose; cellulose hydrates; albumin; dextran gels; glycol monostearate and distearate; synthetic polymers, such as PVP/VA (vinylpyrrolidone/vinyl acetate copolymers), polystyrene or polyvinylpyrrolidone; and hydroxyethylcelluloses or hydroxmethylcelluloses.

The reaction mixture can contain alkalising agents, such as sodium hydroxide, monoethanolamine, triethanolamine, acid or neutral carbonates or phosphates of alkali metals or of alkaline earth metals, or metasilicates, or acidifying agents, such as citric acid, lactic acid, tartaric acid, hydrochloric acid or acetic acid.

The above-mentioned cosmetic ingredients can be introduced either at the start of the reaction, or at any time during the reaction, or also just before carrying out freezing or lyophilisation. If a phase separation occurs during the reaction, one of the above-mentioned solvents, or mixtures thereof, should be added, before freezing, in a sufficient amount to dissolve the phase which has separated out.

The reaction is carried out in an anaerobic medium obtained, for example, by sweeping or bubbling nitrogen, argon or another inert gas, with or without stirring.

The polyhydroxybenzenes are suitably used in an amount of 0.01 to 15%, preferably 0.5 to 5%, by weight, of the total reaction mixture, and the oxidative precursors of the para type are suitably used in an amount of 0.005 to 10%, preferably 0.01 to 8%, by weight, of the total reaction mixture.

The molar ratio (polyhydroxybenzene)/(oxidative dyestuff precursor of the para type), that is to say the ratio (a)/(b), can vary within wide limits in the initial reaction mixture. The ratio is generally from 0.1 to 10 and preferably from 0.5 to 2. For given temperature and time conditions, and depending on the point at which the reaction is stopped by freezing, the final ratio (a)/(b) can also vary within wide limits, the final ratio not necessarily being identical to the initial ratio.

If the initial molar ratio (a)/(b) is greater than 1, the lyophilised mixture contains an excess of polyhydroxybenzene (a), and this increases the strength of the background colour of the dye.

If the ratio (a)/(b) is less than 1, the lyophilisate contains an excess of precursor (b), and, in this case, one or more couplers can be introduced in suitable amounts when the compositions are prepared or applied, the compositions then being applied in the presence of an oxidising agent which is not added until the time of use.

Because the reaction has been stopped at a chosen stage of the reversible reaction and because of the choice of the initial (a)/(b) ratio, the compositions of the invention make it possible to obtain a wider variety of background and shade of the colouration than with the compositions known hitherto.

The reaction is stopped at the desired stage by rapid freezing at a temperature which is generally equal to or less than $-30°$ C., preferably a temperature of $-40°$ to $-70°$ C., and the reaction mixture thus obtained is lyophilised under the usual conditions involving sublimation or desorption. For example, a "USIFROID SMJ" apparatus (RIEUTORD PROCESS), with a condenser inside the vat, can be used. Sublimation is achieved at a temperature below $-30°$ C., preferably below $-35°$ C., under a pressure which is equal to or less than 0.1 mm Hg.

Lyophilisation is suitably carried out on the product spread as a thin layer, and desorption is carried out at a temperature of, say, 15° C. to 60° C. under a pressure of, say, 0.01 mm Hg.

Under these conditions, the total lyophilisation time generally varies from 20 hours to 48 hours. The lyophilised product can thus be obtained in the form of a powder possessing a very high specific surface area, and this facilitates its dissolution at the time of use.

The resulting lyophilisate contains either solely the residual initial reactants and their reaction products, or the initial reactants in the presence of the cosmetic ingredients as defined above, which are also lyophilised. This pulverulent lyophilisate is then stored in an anaerobic medium or immediately packaged, still under an inert atmosphere, in a leaktight package.

According to the invention, composite powders can also be prepared which contain, on the one hand, the above mentioned lyophilisate, and, on the other hand, pulverulent cosmetic ingredients which are non-oxidisable and compatible with the abovementioned lyophilisate. These cosmetic ingredients can be similar to the cosmetic ingredients which have been introduced before lyophilisation. Amongst these ingredients, there may be mentioned, in particular, direct dyestuffs, such as nitro benzene dyestuffs, azo dyestuffs, anthraquinone dyestuffs, indoanilines, indophenols or indamines, thickeners, surface active agents, polymers, perfumes and alkalising or acidifying agents.

Amongst the alkalising agents, there may be mentioned: ammonia, alkylamines, alkanolamines, such as mono-, di- or tri-ethanolamine, alkylalkanolamines, such as aminomethylpropanol or aminomethylpropanediol, sodium hydroxide or potassium hydroxide and ammonium carbonate, sodium carbonate or potassium carbonate, it being possible for these compounds to be used singly or as a mixture.

Amongst the acidifying agents, there may be mentioned: hydrochloric, acetic, citric, tartaric, maleic and phosphoric acids and mixtures thereof.

A first embodiment of the invention involves the application of a self-oxidising composition which can be used directly. Firstly a solution A is prepared, which contains a solvent or a mixture of solvents, such as ethyl, butyl, isopropyl, benzyl and phenylethyl alcohols, glycols or glycol ethers, such as ethylene glycol, propylene glycol, butylglycol and mono-, di- and triethylene glycol monoalkyl ethers, such as ethylene glycol monomethyl ether, ethylene glycol monoethyl ether and diethylene glycol monoethyl ether, and also aqueous mixtures thereof, optionally in the presence of other ingredients of the composition, and the pH is adjusted to 3 to 11 and preferably 6 to 10. The concentration of the above-mentioned solvents is up to 50%, preferably from 2 to 25%, by weight. The lyophilisate or the composite powder is then introduced into the solution A, generally in an amount of 2 to 20%, preferably 8 to 15%, by weight, these amounts being such that the lyophilisate or the composite powder is dissolved in the mixture. The most diverse cosmetic ingredients forming part of the composition, including direct dyestuffs such as those mentioned above, can also be introduced into the mixture.

The cosmetic composition thus prepared is then applied to the hair, generally for 10 to 45 minutes, preferably 20 to 30 minutes, at ambient temperature or under an artificial source of heat. The hair is then rinsed, if desired, shampooed, and rinsed again, and dried.

A second embodiment involves the application of a composition analogous to the abovementioned composition but in which the dyeing operation is completed by the application of an oxidising solution which acts as a developer, this being applied optionally after rinsing out the dyeing composition. A cosmetic composition similar to the above is prepared and, after having applied it to the hair under conditions similar to the abovementioned conditions, the head of hair is optionally rinsed and an oxidising solution B, acting as a developer, is applied. Such a solution contains, in particular, in aqueous solution, hydrogen peroxide, per-salts, potassium ferricyanide or urea peroxide, and, optionally, fatty alcohols and/or oxyethyleneated fatty alcohols.

After the application of the oxidising solution for, say, 5 to 10 minutes, the head of hair is rinsed, optionally shampooed and rinsed again, and dried.

A third embodiment involves the application of a composition comprising a lyophilisate or a composite powder containing an access of oxidative dyestuff precursor of the para type, to which composition suitable amounts of an oxidising agent and of one or more couplers are added before application to the hair. For this purpose, the lyophilisate or the composite powder is dissolved in a solution, such as a solution A mentioned above, and the resulting solution is mixed with an oxidising solution B and with couplers typically chosen from the following classes: meta-phenylenediamines, mono- and di-phenols, meta-aminophenols, napthols, heterocyclic derivatives, in particular derivatives of morpholine or of pyridine, and diketone compounds, or with other cosmetic ingredients, as in the first embodiment, the pH being adjusted to 3 to 11 and preferably 6 to 10. The composition thus obtained is applied to the hair, generally for 15 to 45 minutes and preferably 20 to 30 minutes. The hair is rinsed, shampooed, rinsed again and dried.

The following Examples further illustrate the present invention; the percentages are by weight and the temperatures are in degrees centigrade.

EXAMPLE 1

The following mixture is prepared:

| | |
|---|---|
| N-($\beta$-Methoxyethyl)-para-phenylenediamine dihydrochloride | 3.82 g |
| 1,2,4-Trihydroxybenzene | 2 g |
| Sodium sulphite | 1 g |
| Complex of polypeptides and of aminoacids derived from proteins, sold under the name "Polypeptide LSN" by the Societe STEPAN | 5 g |
| Dioxane | 50 g |
| Neutral sodium carbonate q.s.p. | pH 8 |
| Water q.s.p | 100 g |

After anaerobic storage for one month at 35° C., equilibrium has virtually been reached and is blocked by sudden cooling of the mixture to −70° C. and lyophilisation involving sublimation at −35° C. under a pressure of 0.01 mm Hg, the total operation taking 36 hours.

The pulverulent lyophilisate thus obtained is then kept in a hermetically sealed flask under a nitrogen atmosphere.

At the time of use, 6 g of the lyophilisate are introduced into 40 g of an aqueous solution A, containing 15% of ethylglycol, and the mixture is applied to hair which has been bleached beforehand.

After 30 minutes, the mixture is rinsed out and the head of hair is shampooed and rinsed; it is coloured deep chestnut.

Analogous results are obtained on replacing the "Polypeptide LSN" by aminoacids, casein hydrolysates, albumin or mixtures thereof.

EXAMPLE 2

The following mixture is prepared:

| | |
|---|---|
| N,N-Bis-($\beta$-hydroxyethyl)-para-phenylenediamine monosulphate | 2.94 g |
| 1,2,4-Trihydroxybenzene | 1.26 g |
| Sodium sulphite | 0.1 g |
| Glycine | 5 g |
| Dioxane | 25 g |
| Sodium hydroxide q.s.p. | pH 8 |
| Water q.s.p. | 100 g |

This mixture is stored in the absence of air for 3 weeks at 45° C.

The homogeneous solution thus obtained is subsequently frozen at a temperature of between −70° and −40° and then lyophilised.

A blue-grey powder is then obtained which is stored in brown flasks under an argon atmosphere.

At the time of use, 5 g of this powder are dissolved in 45 g of the following mixture.

| | |
|---|---|
| "Carbopol 934" (an acrylic acid polymer having a molecular weight of 2 to 3 million) | 2 g |
| Butylglycol | 8 g |
| Neutral sodium carbonate q.s.p. | pH 8 |
| Water q.s.p. | 100 g |

This composition is immediately applied to blond hair containing a high percentage of white hair.

After 30 minutes, the composition is rinsed out and the head of hair is then dried; it is coloured ashen deep grey.

EXAMPLE 3

The following mixture is prepared:

| | |
|---|---|
| N,N-Bis-($\beta$-hydroxyethyl)-para-phenylenediamine monosulphate | 8.82 g |
| 1,2,4-Trihydroxybenzene | 3.78 g |
| Glucose | 10 g |
| Sodium hydroxide q.s.p. | pH 8 |
| Water q.s.p. | 100 g |

An oily precipitate rapidly appears at ambient temperature and, after storage for 3 days in an anaerobic medium, 50 g of dioxane are introduced and the homogeneous solution thus obtained is immediately frozen and lyophilised to give a powder.

Before use, 4 g of the abovementioned grey powder are dissolved in 50 g of an aqueous solution A, containing 3 g % of ethylglycol, and the resulting solution is applied to blond hair containing a high percentage of white hair.

After 25 minutes, the head of hair is copiously rinsed and the following oxidising mixture B is applied for 5 minutes:

| | |
|---|---|
| Oxyethyleneated lanoline fatty alcohol containing 10 mols of E.O. (ethylene oxide), sold under the name POLYCHOL by the Société CRODA | 5 g |
| Stearyl alcohol | 5 g |
| 30% strength hydrogen peroxide | 20 g |
| Phosphoric acid q.s.p. | pH 3 |
| Water q.s.p. | 100 g |

This application is followed by rinsing and shampooing. After drying, the hair is coloured deep grey with a dull sheen. The strength of the resulting colouration is analogous to that obtained in Example 2.

Analogous results are obtained on replacing the glucose by lactose, sorbitol, maltose, dextran gels or cellulose hydrates.

EXAMPLE 4

The following mixture is prepared:

| | |
|---|---|
| Para-aminophenol | 1 g |
| 2,4,5-Trihydroxytoluene | 1.4 g |
| Tert.-butyl alcohol | 40 g |
| Neutral sodium carbonate q.s.p. | pH 8 |
| Sodium sulphite | 0.2 g |
| Water q.s.p. | 100 g |

50 g of this mixture are stored in the absence of air for 5 weeks at 45° C.

2.5 g of glycylglycine are then dissolved therein and the resulting mixture is solidified by cooling rapidly to −50° C., this being followed by lyophilisation.

At the time of use, 3 g of the lyophilisate are dissolved in 50 g of an aqueous solution A, containing 10% of ethanol and 10% of butylglycol, and the resulting solution is then applied for 25 minutes to light blond hair containing about 60% of white hair.

After rinsing and drying, the head of hair is coloured blond with an attractive golden sheen.

EXAMPLE 5

The following mixture is prepared:

| | |
|---|---|
| N-Ethyl-N-mesylaminoethyl-para-phenylenediamine dihydrochloride | 3.30 g |
| 1,2,4-Trihydroxybenzene | 1.26 g |
| Ascorbic acid | 1 g |
| "Polypeptide LSN" prepared by the Societe STEPAN | 5 g |
| Sodium hydroxide q.s.p. | pH 8 |
| Water q.s.p. | 100 g |

This mixture is stored in the absence of air for 2 days at 45° C.

The oily precipitate formed is redissolved by adding 75 g of dioxane to the mixture. By adding citric acid, the pH of this mixture is lowered to 4–5 and the mixture is rapidly frozen and then lyophilised to give a powder.

At the time of use, 6 g of the light grey lyophilised powder thus obtained are dissolved in 45 g of an aqueous solution A, containing 15 g % of ethylglycol and adjusted to pH 9 with monoethanolamine.

This solution is applied for 20 minutes to an initially white head of hair and, after rinsing, the oxidising solution B of Example 3 is applied for 10 minutes.

After rinsing, shampooing and drying, the hair is coloured silver-grey.

EXAMPLE 6

The following mixture is prepared:

| | |
|---|---|
| N-Ethyl-N-(β-piperidinoethyl)-para-phenylene-diamine dihydrochloride | 6.4 g |
| 2,4,5-Trihydroxytoluene | 2.8 g |
| Dioxane | 50 g |
| Sodium sulphite | 0.3 g |
| Neutral sodium carbonate q.s.p. | pH 8.5 |
| Water q.s.p. | 100 g |

This mixture is stored in the absence of air and at 45° C. for one month.

10 g of glycocoll are then rapidly incorporated and the resulting mixture is solidified by cooling to −60° C., followed by lyophilisation.

At the time of use, 5 g of the resulting lyophilisate are dissolved in 45 g of an aqueous solution A, containing 20% of ethyl alcohol, and the resulting solution is applied for 30 minutes to a blond head of hair containing 20% of white hair.

After rinsing and drying, the hair is coloured pearlescent light chestnut.

Analogous results are obtained on replacing the dioxane by cyclohexanol in the reaction mixture.

EXAMPLE 7

The following mixture is prepared:

| | |
|---|---|
| 2,6-dimethyl-5-methoxy-para-phenylenediamine dihydrochloride | 2.40 g |
| 1,2,4-Trihydroxybenzene | 1.26 g |
| Formamidinesulphinic acid | 1 g |
| Glycylglycine | 5 g |
| Tert.-butyl alcohol | 45 g |
| Neutral sodium carbonate q.s.p. | pH 8 |
| Water q.s.p. | 100 g |

This solution is stored in the absence of air for one week and then lyophilised.

At the time of use, 5 g of this lyophilisate are introduced into 45 g of the following solution A, containing:

| | |
|---|---|
| Ethylglycol | 10 g |
| Absolute ethyl alcohol | 10 g |
| Triethanolamine q.s.p. | pH 9 |
| Water q.s.p. | 100 g |

The 50 g of the mixture thus obtained are then incorporated with 50 g of a solution B, consisting of a cosmetic milk containing 6% of hydrogen peroxide, and the resulting mixture is then applied for 30 minutes to light chestnut hair which, after rinsing, shampooing and drying, has an attractive purple-violet sheen.

EXAMPLE 8

The following mixture is prepared:

| | |
|---|---|
| N-Ethyl-N-(β-piperidinoethyl)para-phenylene-diamine dihydrochloride | 3.56 g |
| 5-Methoxy-1,2,4-trihydroxybenzene | 1.56 g |
| Dioxane | 25 g |
| "Polypeptide LSN" prepared by the Societe STEPAN | 6 g |

-continued

| Sodium sulphite | 1 g |
| --- | --- |
| Sodium hydroxide q.s.p. | pH 8 |
| Water q.s.p. | 100 g |

After storage for one month at 45° C. in the absence of air, the reaction is blocked by rapid cooling of the mixture and lyophilisation.

At the time of use, 6 g of this lyophilisate are introduced into 45 g of the following mixture A, containing:

| "Carbopol 934" | 2 g |
| --- | --- |
| Ethylglycol | 15 g |
| Neutral sodium carbonate q.s.p. | pH 8 |
| Water q.s.p. | 100 g |

The latter mixture obtained is then applied to a very light blond head of hair containing a high percentage of white hair.

After an application time of 20 minutes, the hair is rinsed and dried; it is uniformly coloured slightly golden blond.

Analogous results are obtained on replacing the ethylglycol by isopropanol in the solvent mixture A.

EXAMPLE 9

A lyophilised powder is prepared as in Example 3.

At the time of use, 4 g of the abovementioned lyophilised powder are introduced into 50 g of the following mixture A:

| 4-Amino-3-nitrophenol | 0.1 g |
| --- | --- |
| "Carbopol 934" | 1.7 g |
| Butylglycol | 8 g |
| Triethanolamine q.s.p. | pH 9 |
| Water q.s.p. | 100 g |

The resulting mixture is applied for 30 minutes to a blond head of hair containing 90% of white hair.

After rinsing, an oxidising mixture B, as prepared in Example 3, is applied to the head of hair for 10 minutes.

After rinsing, shampooing and drying, the hair is coloured chestnut.

Analogous results are obtained on replacing the hydrogen peroxide by per-salts or urea peroxide in the oxidising mixture B.

EXAMPLE 10

The following mixture is prepared:

| 2,6-Dimethyl-5-methoxy-para-phenylenediamine dihydrochloride | 2.4 g |
| --- | --- |
| 2,4,5-Trihydroxytoluene | 1.4 g |
| Tert.-butyl alcohol | 20 g |
| Dioxane | 30 g |
| Vinylpyrrolidone/vinyl acetate copolymer (60/40) | 2 g |
| Sodium sulphite | 0.09 g |
| Sodium hydroxide q.s.p. | pH 8 |
| Water q.s.p. | 100 g |

After storage in an anaerobic medium for 3 weeks at 45° C., the abovementioned reaction mixture is rapidly frozen at −40° C. and lyophilised.

At the time of use, 6 g of the abovementioned lyophilisate are dissolved in 45 g of an aqueous solution A, containing 15% of ethylglycol, and the resulting solution is applied for 20 minutes to a light chestnut head of hair.

After rinsing, the oxidising solution B of Example 3 is applied to the head of hair for 10 minutes; the hair is rinsed and dried and has an attractive pink sheen.

In the preceeding examples the reversible reaction is stopped at the desired stage preferably after a chromatographic control.

We claim:

1. Process for the preparation of a composition suitable for use in dyeing human hair, which comprises the following steps in sequence: (1) reacting in an anaerobic medium (a) at least one polyhydroxybenzene of the formula:

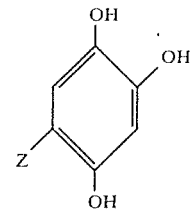

in which Z denotes an alkoxy or alkyl radical containing 1 to 4 carbon atoms or a hydrogen atom, and (b) at least one oxidative dyestuff precursor of the para type in a first solvent, said first solvent being dioxane, tert.-butyl alcohol, benzyl alcohol, cyclohexanol or a mixture or aqueous solution thereof, or solvents which do not give eutectics with water; (2) freezing the reaction to obtain a reaction mixture containing said at least one polyhydroxybenzene, said at least one oxidative dyestuff precursor of the para type and at least one leuco derivative; (3) lyophilising the reaction mixture thereby removing the first solvent; and (4) dissolving the lyophilised product of step (3) in a second solvent, said second solvent being ethyl, butyl, isopropyl, benzyl or phenylethyl alcohol, ethylene glycol, propylene glycol, butylglycol or a mono-, di- or tri-ethylene glycol monoalkyl ether, or an aqueous mixture thereof.

2. Process according to claim 1, in which step (1) is carried out at a temperature of 10° C. to the reflux temperature of the first solvent, from a few hours to several weeks and at a pH of 3 to 11.

3. Process according to claim 2 in which step (1) is carried out at 20° to 50° C. at a pH of 5 to 9.

4. Process according to claim 1 in which the oxidative dyestuff precursor of the para type has the formula:

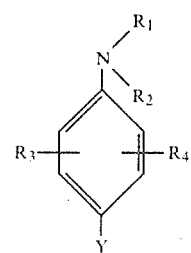

in which
Y denotes: either a group OH, if $R_1$, $R_2$ and $R_3$ simultaneously denote a hydrogen atom, $R_4$ denoting a hydrogen atom or an alkyl radical, or Y denotes a $NH_2$ group if:

R₁ and R₂, which are identical or different, denote a hydrogen atom or an alkyl, hydroxyalkyl or alkoxyalkyl radical, or R₁ denotes a hydrogen atom or an alkyl radical and R₂ denotes an alkoxy, carbamylalkyl or mesylaminoalkyl radical, an aminosulphonylalkyl radical in which the nitrogen atom is optionally substituted, a piperidinoalkyl or morpholinoalkyl radical or a phenyl nucleus, or R₁ and R₂ form, together with the nitrogen atom to which they are attached, a heterocyclic ring;

R₃ denotes a hydrogen atom, an alkyl radical or the radical —OR₅, in which R₅ represents an hydroxyalkyl or alkoxyalkyl group; and R₄ denotes a hydrogen atom or an alkyl radical, or a salt thereof, the alkyl radicals containing 1 to 4 carbon atoms.

5. Process according to claim 1 in which the polyhydroxybenzene is used in an amount of 0.01 to 15% by weight, and the oxidative dyestuff precursor of the para type is used in an amount of 0.005 to 10% by weight, relative to the weight of the reaction mixture.

6. Process according to claim 5 in which the polyhydroxybenzene is used in an amount of 0.5 to 5% by weight and the oxidative dyestuff precursor is used in an amount of 0.01 to 8% by weight, relative to the weight of the reaction mixture.

7. Process according to claim 1 in which the molar ratio of polyhydroxybenzene to oxidative dyestuff precursor of the para type is from 0.1 to 10.

8. Process according to claim 7 in which the said molar ratio is from 0.5 to 2.

9. Process according to claim 1 in which a direct dyestuff and/or other cosmetic ingredient compatible with the reaction mixture are introduced into the reaction mixture.

10. Process according to claim 1 in which an inorganic or organic filler which is soluble in the reaction medium is added in an amount of 2 to 20% by weight, relative to the weight of the reaction medium, at the start or at the end of step (1).

11. Process according to claim 10 in which the filler is an aminoacid or polypeptide, casein hydrolysate, carbohydrate, a cellulose hydrate, albumin, dextran gel, glycol monostearate or distearate, a synthetic polymer, a hydroxyethylcellulose or hydroxymethylcellulose.

12. Process according to claim 1 in which a reducing agent is added, in an amount of 0.01 to 5% by weight, relative to the weight of the reaction medium, at the start or at the end of step (1) or to the lyophilisate.

13. Process according to claim 12 in which the reducing agent is the dithionite, bisulphite or sulphite of sodium, potassium or ammonium, ascorbic acid or an ester or salt thereof, formamidinesulphinic acid, thiomalic acid or cysteine or a salt thereof.

14. Process according to claim 1 in which step (1) is stopped such that the ratio (a)/(b), in the lyophilisate is less than 1.

15. A composite powder which comprises a composition obtained by a process as claimed in claim 1 and at least one of a direct dyestuff and a cosmetic ingredient which is compatible with the composition.

16. A powder according to claim 15 which is stored or packaged in an inert atmosphere.

17. A composition obtained by a process as claimed in claim 1 which is stored or packaged in an inert atmosphere.

18. A process for dyeing human hair which comprises dissolving, at the time of use, a composition obtained by a process which comprises the following steps in sequence: (1) reacting in an anaerobic medium (a) at least one polyhydroxybenzene of the formula:

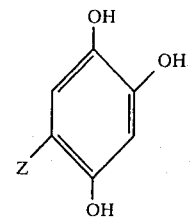

in which Z denotes an alkoxy or alkyl radical containing 1 to 4 carbon atoms or a hydrogen atom, and (b) at least one oxidative dyestuff precursor of the para type in a first solvent, said first solvent being dioxane, tert.-butyl alcohol, benzyl alcohol, cyclohexanol or a mixture or aqueous solution thereof, or solvents which do not give eutectics with water; (2) freezing the reaction to obtain a reaction mixture containing said at least one polyhydroxybenzene, said at least one oxidative dyestuff precursor of the para type and at least one leuco derivative; (3) lyophilising the reaction mixture thereby removing the first solvent, in a second solvent, said second solvent being ethyl, butyl, isopropyl, benzyl or phenylethyl alcohol, ethylene glycol, propylene glycol, butylglycol or a mono-, di- or tri-ethylene glycol monoalkyl ether, or an aqueous mixture thereof, and applying the resulting solution to the hair.

19. A process according to claim 18 in which the solution is applied to the hair for 10 to 45 minutes at ambient temperature, and the hair is then rinsed, shampooed, rinsed again and dried.

20. Process according to claim 19 in which the solution is applied for 20 to 30 minutes.

21. A process according to claim 18 in which the composition is introduced, in an amount of 2 to 20%, by weight, into the second solvent and the pH is adjusted to 3 to 11.

22. A process according to claim 21 in which the composition is introduced, in an amount of 8 to 15% by weight, into the second solvent and the pH is adjusted to 6 to 10.

23. A process according to claim 21 in which a direct dyestuff, thickener, surface-active agent, polymer, perfume or acidifying or alkalising agent is introduced into the solution.

24. A process according to claim 18 in which, after the solution is applied to the hair and optionally after rinsing, an oxidising solution is applied to the hair for 5 to 10 minutes and the hair is then rinsed, optionally shampooed and rinsed and then dried.

25. A process according to claim 18 in which the solution is obtained from a said composition in which the ratio (a)/(b) is less than 1, and an oxidising solution and one or more couplers are introduced into the solution before application to the hair, the pH of the solution being 3 to 11.

26. A process according to claim 25 in which the pH of the said solution is 6 to 10.

27. A process according to claim 26 in which the coupler is a meta-phenylenediamine, mono- or di-phenol, meta-aminophenol, naphthol, heterocyclic derivative or a diketone.

* * * * *